(12) United States Patent
Grasso, III et al.

(10) Patent No.: US 7,104,983 B2
(45) Date of Patent: Sep. 12, 2006

(54) LASER LITHOTRIPSY DEVICE WITH SUCTION

(75) Inventors: Michael Grasso, III, Rye, NY (US); Douglas Goodshall, Franklin, MA (US); Clifford Liu, Randolph, MA (US); Anthony Tremaglio, Hopkington, MA (US); George Bourne, Southborough, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 155 days.

(21) Appl. No.: 10/801,128

(22) Filed: Mar. 16, 2004

(65) Prior Publication Data

US 2004/0243123 A1 Dec. 2, 2004

Related U.S. Application Data

(60) Continuation of application No. 10/099,481, filed on Mar. 15, 2002, now Pat. No. 6,726,681, which is a division of application No. 09/507,029, filed on Feb. 18, 2000, now Pat. No. 6,375,651.

(60) Provisional application No. 60/120,666, filed on Feb. 19, 1999.

(51) Int. Cl.
 *A61B 18/18* (2006.01)

(52) U.S. Cl. .................. 606/15; 606/17; 606/18

(58) Field of Classification Search ............... 606/41, 606/45, 46, 48–50, 1, 15–18; 604/113–114
See application file for complete search history.

(56) References Cited

U.S. PATENT DOCUMENTS

| | | | |
|---|---|---|---|
| 3,823,717 A | 7/1974 | Pohlman et al. | |
| 3,941,121 A | 3/1976 | Olinger et al. | |
| 4,146,019 A | 3/1979 | Bass et al. | |
| 4,445,892 A | 5/1984 | Hussein et al. | |
| 4,662,368 A | 5/1987 | Hussein et al. | |
| 4,672,961 A | 6/1987 | Davies | |
| 4,693,556 A | 9/1987 | McCaughan, Jr. | |
| 4,800,876 A | 1/1989 | Fox et al. | |
| 4,836,189 A | 6/1989 | Allred, III et al. | |
| 4,838,246 A | 6/1989 | Hahn et al. | |
| 4,852,567 A | 8/1989 | Sinofsky | |
| 4,887,600 A | 12/1989 | Watson et al. | |
| 4,927,426 A | 5/1990 | Dretler | |
| 4,932,954 A | 6/1990 | Wondrazek et al. | |
| 4,960,108 A | 10/1990 | Reichel et al. | |
| 4,963,142 A | 10/1990 | Loertscher | |
| 4,968,314 A | 11/1990 | Michaels | |

(Continued)

FOREIGN PATENT DOCUMENTS

WO     WO 89/12479     12/1989

(Continued)

OTHER PUBLICATIONS

Grasso et al., "Retrograde Ureteropyeloscopic Treatment of 2 CM. or Greater Upper Urinary Tract and Minor Staghorn Calculi," Reprinted from *The Journal of Urology*, vol. 160, Aug. 1998, pp. 346-351.

(Continued)

*Primary Examiner*—Roy D. Gibson
(74) *Attorney, Agent, or Firm*—Finnegan, Henderson, Farabow, Garrett & Dunner, LLP

(57) ABSTRACT

A medical device is provided which comprises a suction conduit and an energy-transmitting conduit wherein at least some of the transmitted energy is directed to the distal region of the suction conduit. The device may include an optical apparatus for directing the energy. The device has applications in lithotripsy and tissue-removal in a patient.

30 Claims, 13 Drawing Sheets

U.S. PATENT DOCUMENTS

| | | | |
|---|---|---|---|
| 4,997,435 A | 3/1991 | Demeter | |
| 5,009,658 A | 4/1991 | Damgaard-Iversen et al. | |
| 5,026,366 A * | 6/1991 | Leckrone | 606/7 |
| 5,041,121 A | 8/1991 | Wondrazek et al. | |
| 5,056,917 A | 10/1991 | Nowacki et al. | |
| 5,059,200 A | 10/1991 | Tulip | |
| 5,071,422 A | 12/1991 | Watson et al. | |
| 5,095,889 A | 3/1992 | Weissmüller et al. | |
| 5,135,534 A | 8/1992 | Tulip | |
| 5,151,096 A | 9/1992 | Khoury | |
| 5,151,098 A | 9/1992 | Loertscher | |
| 5,176,675 A | 1/1993 | Watson et al. | |
| 5,222,952 A | 6/1993 | Loertscher | |
| 5,224,942 A | 7/1993 | Beuchat et al. | |
| 5,239,982 A | 8/1993 | Trauthen | |
| 5,242,437 A | 9/1993 | Everett et al. | |
| 5,242,438 A | 9/1993 | Saadatmanesh et al. | |
| 5,242,454 A | 9/1993 | Gundlach et al. | |
| 5,257,991 A | 11/1993 | Fletcher et al. | |
| 5,281,231 A | 1/1994 | Rosen et al. | |
| 5,298,026 A | 3/1994 | Chang | |
| 5,304,228 A | 4/1994 | Prince | |
| 5,312,399 A * | 5/1994 | Hakky et al. | 606/15 |
| 5,312,418 A | 5/1994 | Bonnet | |
| 5,324,282 A | 6/1994 | Dodick | |
| 5,342,350 A | 8/1994 | Amiel | |
| 5,343,543 A | 8/1994 | Novak, Jr. et al. | |
| 5,343,874 A | 9/1994 | Picha et al. | |
| 5,366,456 A | 11/1994 | Rink et al. | |
| 5,370,649 A | 12/1994 | Gardetto et al. | |
| 5,379,779 A | 1/1995 | Rowland et al. | |
| 5,380,317 A | 1/1995 | Everett et al. | |
| 5,395,361 A | 3/1995 | Fox et al. | |
| 5,416,878 A | 5/1995 | Bruce | |
| 5,425,735 A | 6/1995 | Rosen et al. | |
| 5,429,596 A | 7/1995 | Arias et al. | |
| 5,437,659 A | 8/1995 | Leckrone | |
| 5,437,660 A | 8/1995 | Johnson et al. | |
| 5,443,470 A | 8/1995 | Stern et al. | |
| 5,449,357 A | 9/1995 | Zinnanti | |
| 5,449,363 A | 9/1995 | Brust et al. | |
| 5,451,216 A | 9/1995 | Quinn | |
| 5,469,524 A | 11/1995 | Esch et al. | |
| 5,476,450 A | 12/1995 | Ruggio | |
| 5,496,306 A | 3/1996 | Engelhardt et al. | |
| 5,496,309 A | 3/1996 | Saadat et al. | |
| 5,505,210 A | 4/1996 | Clement | |
| 5,536,234 A | 7/1996 | Newman | |
| 5,551,448 A | 9/1996 | Matula et al. | |
| 5,562,640 A | 10/1996 | McCabe et al. | |
| 5,562,658 A | 10/1996 | Long | |
| 5,588,952 A | 12/1996 | Dandolu | |
| 5,626,560 A | 5/1997 | Söring | |
| 5,642,370 A | 6/1997 | Mitchell et al. | |
| 5,643,250 A | 7/1997 | O'Donnell, Jr. | |
| 5,644,585 A | 7/1997 | Mitchell et al. | |
| 5,667,475 A | 9/1997 | Laser et al. | |
| 5,681,336 A | 10/1997 | Clement et al. | |
| 5,718,709 A | 2/1998 | Considine et al. | |
| 5,722,980 A | 3/1998 | Schulz et al. | |
| 5,728,129 A | 3/1998 | Summers | |
| 5,733,298 A | 3/1998 | Berman et al. | |
| 5,741,244 A | 4/1998 | Klaas | |
| 5,746,736 A | 5/1998 | Tankovich | |
| 5,749,887 A | 5/1998 | Heske et al. | |
| 5,860,972 A | 1/1999 | Hoang | |
| 5,897,551 A | 4/1999 | Everett et al. | |
| 5,906,611 A | 5/1999 | Dodick et al. | |
| 5,938,645 A | 8/1999 | Gordon | |
| 5,941,869 A | 8/1999 | Patterson et al. | |
| 5,957,914 A | 9/1999 | Cook et al. | |
| 5,999,686 A | 12/1999 | Leaman | |
| 6,017,339 A | 1/2000 | Sadamasa | |
| 6,056,743 A | 5/2000 | Ellis et al. | |
| 6,068,603 A * | 5/2000 | Suzuki | 600/565 |
| 6,296,638 B1 * | 10/2001 | Davison et al. | 606/41 |

FOREIGN PATENT DOCUMENTS

| | | |
|---|---|---|
| WO | WO 90/05562 A1 | 5/1990 |
| WO | WO 95/24867 A1 | 10/1995 |
| WO | WO 96/32895 A2 | 10/1996 |
| WO | WO 96/32895 A3 | 10/1996 |

OTHER PUBLICATIONS

Grasso et al., "Small Diameter, Actively Deflectable, Flexible Ureteropyeloscopy," *The Journal of Urology*, vol. 160, Nov. 1998, pp. 1648-1654.

Grasso, III, M.D., "Chapter 32—Flexible Fiberoptic Ureteropyeloscopy," *Smith's Textbook of Endourology*, vol. 1, 1996, Quality Medical Publishing Inc., pp. 443-454.

Grasso, Michael, "Chapter 10—Intracorporeal Lithotripsy: Ultrasonic, Electrohydraulic, Laser, and Electromechanical," *Textbook of Operative Urology*, 1994, Fray F. Marshall (ed.) W.B. Saunders Co., pp. 77-89.

Grasso, Michael, "Experience with the Holmium Laser as an Endoscopic Lithotrite," *Urology*, vol. 48, No. 2, 1996, pp. 199-206.

Matsuoka, M.D., et al., "Holmium: Yttrium-Aluminum-Garnet Laser For Endoscopic Lithotripsy," Urology®, vol. 45, No. 6, Jun. 1995, pp. 947-952.

Stoller et al., "Ureteroscopy Without Routine Balloon Dilation: An Outcome Assessment," *The Journal of Urology*, vol. 147, May 1992, pp. 1238-1242.

Bagley et al., "Ureteral Laser Lithotripsy Using teh Pusolith," *Journal of Endourology*, vol. 3, No. 1, 1989, pp. 91-98.

Grasso et al., "Flexible Ureteroscopic Lithotripsy Using Pulsed-Dye Laser," *Journal of Endourology*, vol. 4, No. 2, 1990, pp. 155-160.

Grasso et al., "Techniques in Endoscopic Lithotripsy Using Pulsed Dye Laser", *Urology*, vol. 37, No. 2, Feb. 1991, pp. 138-144.

Grasso et al., "Pulsed Dye Laser Lithotripsy-Currently Applied to Urological and Biliary Calculi," *Journal of Clinical Laser Medicine & Surgery*, Oct. 1991, pp. 355-359.

Grasso et al., "An Endoscopic Estimate of Calculus Composition Directing Laser Lithotripsy Techniques," *Journal of Endourology*, vol. 6, No. 5, 1992, pp. 331-333.

Grasso et al., "Shock Wave Lithotripsy Failures Treated with Endoscopic Laser Lithotripsy," *Journal of Endourology*, vol. 6, No. 5, 1992, pp. 335-339.

Grasso et al., "Endoscopic Pulsed Dye-Laser Litotripsy: 159 Consecutive Cases," *Journal of Endourology*, vol. 8, No. 1, 1994, pp. 25-27.

Grasso et al., "Endoscopic Management of the Symptomatic Caliceal Diverticular Calculus," *The Journal of Urology*, vol. 153, Jun. 1995, pp. 1878-1881.

Loisides et al., "Mechanical Impactor Employing Nitinol Probes to Fragment Human Calculi: Fragmentation Efficiency with Flexible Endoscopic Deflection," *Journal of Endourology*, vol. 9, No. 5, Oct. 1995, pp. 371-374.

Tawfiek et al., "Initial Use of Browne Pneumatic Impactor," *Journal of Endourology*, vol. 11, No. 2, Apr. 1997, pp. 121-124.

Grasso et al., "Principle and Applications of Laser Lithotripsy: Experience with the Holmium Laser Lithotrite," *Journal of Clinical Laser Medicine & Surgery*, vol. 16, No. 1, 1998, pp. 3-7.

Grasso, "Ureteroscopic Lithotripsy," *Current Opinion in Urology*, vol. 9, 1999, pp. 329-333.

Sullivan et al., "Transhepatic Laser Lithotripsy of Choledocholithiasis: Initial Clinical Experience," *J.V.I.R.*, vol. 2, No. 3, Aug. 1991, pp. 387-391.

Grasso, "Laser Fragments Calculi After ESWL Failure," *Urology Times*, vol. 20, No. 5, 1992, p. 2.

Microvasive Boston Scientific Corporation, "Percutaneous Nephrolithotomy," *Viewpoint Techniques in Endourology*, 1995, pp. 1-10.

The American Urological Association, "What are Ureteral Stones?," *American Urological Association, Inc.*, 1997, pp. 1-8.

LeRoy, "Chapter 14—Percutaneous Access," *Smith's Textbook of Endourology*, Quality Medical Publishing, Inc., vol. 1, 1996, pp. 199-210.

Denstedt et al., "The Swiss Lithocast: A New Device for Intracorporeal Lithotripsy," *The Journal of Urology*, vol. 148, Sep. 1992, pp. 1088-1090.

Grasso, M.D. et al., "The Case for Primary Endoscopic Management of Upper Urinary Tract Calculi: I. A Critical Review of 121 Extracorporeal Shock-Wake Lithotripsy Failures," *Urology®*, vol. 45, No. 3, Mar. 1995, pp. 363-371.

Grasso, M.D. et al., "The Case for Primary Endoscopic Management of Upper Urinary Tract Calculi: II. Cost and Outcome Assessment of 112 Primary Ureteral Calculi," *Urology®*, vol. 45, No. 3, Mar. 1995, pp. 372-376.

* cited by examiner

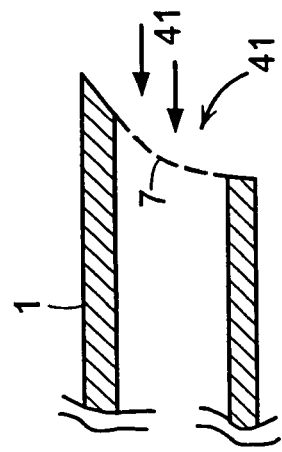
FIG. 2A
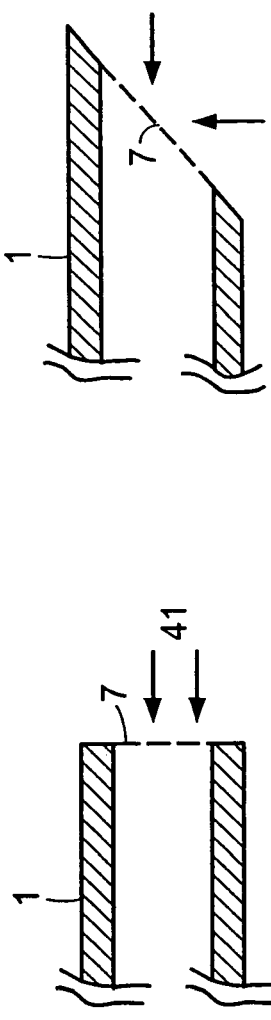
FIG. 2B
FIG. 2C
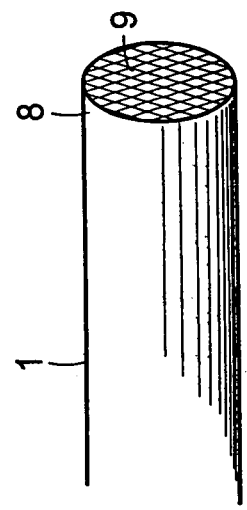
FIG. 2E
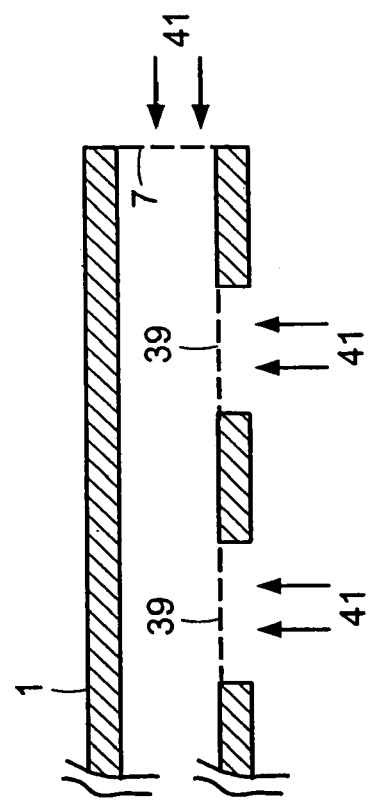
FIG. 2D

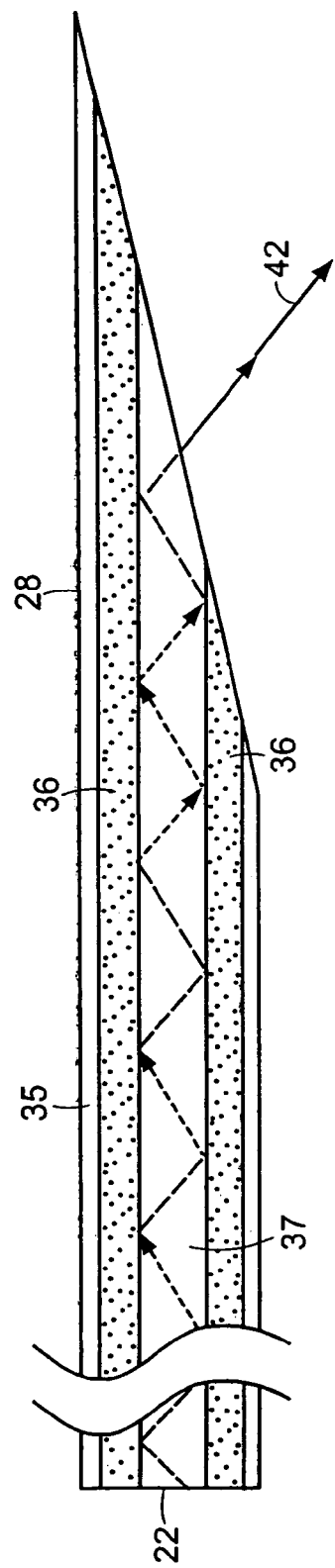
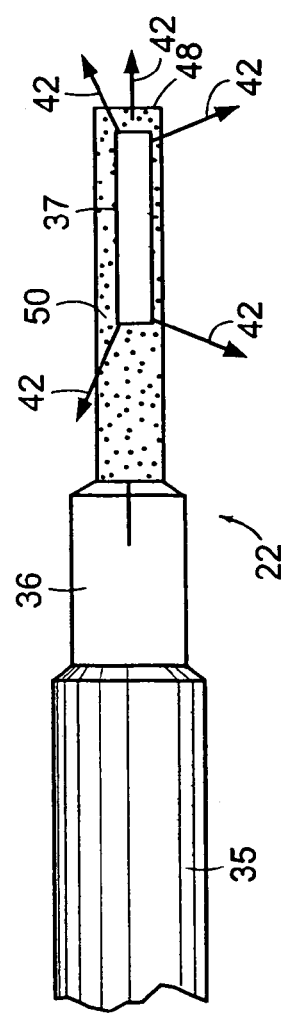
FIG. 7A
FIG. 7B

LASER LITHOTRIPSY DEVICE WITH SUCTION

CROSS-REFERENCE TO RELATED APPLICATIONS

This application is a continuation of U.S. patent application Ser. No. 10/099,481, filed Mar. 15, 2002, now U.S. Pat. No. 6,726,681, which is a divisional of U.S. patent application Ser. No. 09/507,029, filed Feb. 18, 2000, now U.S. Pat. No. 6,375,651, which claims the benefit of U.S. provisional application No. 60/120,666 filed Feb. 19, 1999, all of which are incorporated herein by reference.

TECHNICAL FIELD

The present invention relates to methods and devices for destroying and removing unwanted materials such as calculi, deposits and tissues (for example, polyps, tumor cells) from body lumens, and more particularly to laser lithotripsy treatment of urinary stones.

BACKGROUND INFORMATION

Open surgical intervention was once the standard treatment for the removal of calculi or stones, especially when such calculi are deposited in a body lumen other than the bladder. But other less invasive techniques have emerged as safe and effective alternatives. Lithotripsy, the crushing of stones that develops in the body into fragments that are easier to remove, is one such technique. Lithotripsy devices have been developed which utilize electrohydraulic probes, ultrasonic probes, electromechanical impactors, or a pin driven by compressed air. These devices typically use percutaneous endoscopic techniques and are configured to be introduced into the body through small puncture sites to avoid open surgical intervention. Focused shock waves can also be delivered from an external source in a non-invasive procedure known as extracorporeal shock wave lithotripsy (ESWL).

Recently, lasers have been used as an alternative source of energy in lithotripsy, especially for the destruction of renal and bilary stones. Lasers are suited for minimally invasive lithotripsy because the diameter of the laser fiber is small and the aperture of the working channel can be minimized. An extensive review of the use of lasers for lithotripsy is provided in the book entitled "Laser Lithotripsy," edited by R. Stein, Springer Verlag, 1988. A fiber optic that travels along the longitudinal axis of a rigid or flexible endoscope typically transmits the laser beam. Various types of laser lithotripsy systems with a variety of laser sources, including pulsed dye laser, alexandrite laser, neodymium laser and holmium laser, have been developed.

A common problem in intracorporeal lithotripsy treatment is the difficulty in restricting target movement. For example, when using pulsed lasers such as the holmium yttrium-aluminum-garnet (Ho:YAG) laser, higher frequency pulsation and higher energy in each pulse produce quicker fragmentation of the stone, but also produce significant stone mobility, which decreases treatment efficiency. Lower frequency to pulsation and lower pulse energy may result in less significant stone mobility, but the treatment time will be prolonged. Regardless of energy level of each emission, stones of smaller sizes present an inherent mobility problem. Incomplete lithotripsy treatment of smaller stones or debris can leave a nidus for future stone growth.

Another problem often encountered by a lithotripsy endoscopist involves the suction tube that is found in some endoscopes. Such a conduit is generally connected to a pump that produces a vacuum when in operation and clogging at distal ends by stones and their fragments has been widely reported. See. e.g. U.S. Pat. No. 4,146,019 to Bass et al. Severe clogging may necessitate repeated removal, cleaning and reinsertion of the endoscope during an operation.

SUMMARY OF THE INVENTION

An object of the present invention is thus to restrict the movement of targets of lithotripsy treatment, especially small stones and stone fragments. Another object of the invention is to remove stone fragments resulting from a lithotripsy treatment in a more complete and immediate manner. Yet another object of the invention is to solve the problem of clogging at the distal region of a suction conduit used in lithotripsy.

The present invention provides devices and related methods for the destruction and removal of unwanted materials such as calculi, deposits and tissues (e.g., polyps and tumor cells) from a patient's body lumen. The invention achieves these objects by combining a suction conduit with a high-energy delivery system such that at least some of the high energy transmitted is directed to a region near the distal end of the suction conduit. For example, some of the energy can be directed inside, outside, at the face of the tip or a combination thereof. As a result, the energy destroys materials stuck at the distal end of the suction conduit and provides the user with a suction device that is equipped with a non-clogging tip.

The devices of the invention comprises a suction conduit connected to a pump for suction and a second conduit connected to an energy source for transmitting high energy. Once the suction conduit is in operation, it keeps stones or stone fragments near its tip, stabilizing the movement of the stone. The second conduit is designed to direct a position of the high energy into, across, and/or outside of the distal end of the suction conduit and thus onto the stones or stone fragments. The energy fragments, pulverizes or erodes stones, including those caught by the force of suction onto the tip of the suction conduit, into smaller parts or dusts, and the suction conduit can instantaneously evacuate the stone debris. For example, in a preferred embodiment where Ho:YAG laser is used as the energy source, the laser energy continues to break down fragments that are still too large to enter the suction conduit while knocking them off the suction tip temporarily thus preventing clogging of the tip. A portion of the energy may also be directed into a portion of the lumen of the suction conduit, thereby preventing clogging that would have occurred after debris entered the conduit.

The devices and methods of the invention take full advantage of the suction force in, removing debris instantaneously from the site of the treatment, allowing a more complete and speedy treatment. Also, by directing a high energy towards the distal region of the suction conduit, the devices point the energy into a region where targets are accumulated and relatively immobilized by the suction. The devices and methods thus offer enhanced treatment efficiency by permitting a more thorough removal of debris and by avoiding operational difficulties associated with a clogged suction conduit.

In one aspect, the devices of the invention can also be equipped with structures such as barriers or shields in the distal region of the suction conduit to help block large particles. In another aspect, the devices of the invention use multiple energy conduits bundled or dispersed in or around the wall of the suction conduit. Yet in another aspect, the devices use multiple conduits bearing indicia or marking that permit their identification during a procedure. In still another aspect, the devices of the invention direct energy towards the distal region of the first suction conduit with or without a separate optical apparatus such as mirrors, lenses, prisms for example.

The devices and methods of the invention can be used for the removal of stones and calcifications throughout the body. First, the device is inserted into the body lumen of a patient and the distal end of the suction conduit is positioned near a stone. Then, a high energy is transmitted by the energy conduits and directed to the distal region of the suction conduit, thereby breaking up stones stuck at the distal region and removing its fragments through suction.

The devices can also be utilized for the removal of soft tissue such as polyps or tumor cells. For example, the device is first inserted into the body lumen of a patient and the distal end of the suction conduit is positioned near the tissue to be removed. Then, a high energy is transmitted by the energy conduits and directed to the distal region of the suction conduit and thereby shearing off the tissue and removing it through suction. Additionally, the devices can be used for orthopedic applications and endoscopic applications such as arthroscopy and endoscopic retrograde cholangio-pancreatiography (ERCP).

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIGS. 2A–2D are longitudinal cross-section views of various embodiments of the distal end of the suction conduit taken along line 6—6 in FIG. 1A.

FIG. 2E is a perspective view of an embodiment of a suction conduit with a mesh-cap in accordance with the subject invention.

FIG. 7A is a schematic longitudinal cross-section view of an angled tip of a laser fiber manufactured by etching.

FIG. 7B is a side view of laser fiber tip applied with a reflective coating in accordance with the invention.

DESCRIPTION

Definition

Distal region: a region near or around, both inside and outside and including an end that is farther away from the origin of attachment.

Conduit: a channel or a tubing for conveying energy or matter.

Detailed Description

The devices and methods of the present invention combine an energy-transmitting means with a suction means to enhance the efficiency of material removal from a body lumen. In doing so, they solve both the problem of calculi mobility and clogging at the distal region of a suction means used in such medical procedures. The devices comprise at least a Suction conduit and a high-energy conduit, and the energy transmitted is at least partly directed to the distal region of the suction conduit. Other elements such as viewing instruments, an illumination means or an irrigation conduit can be further combined with these elements.

Figure 1A:
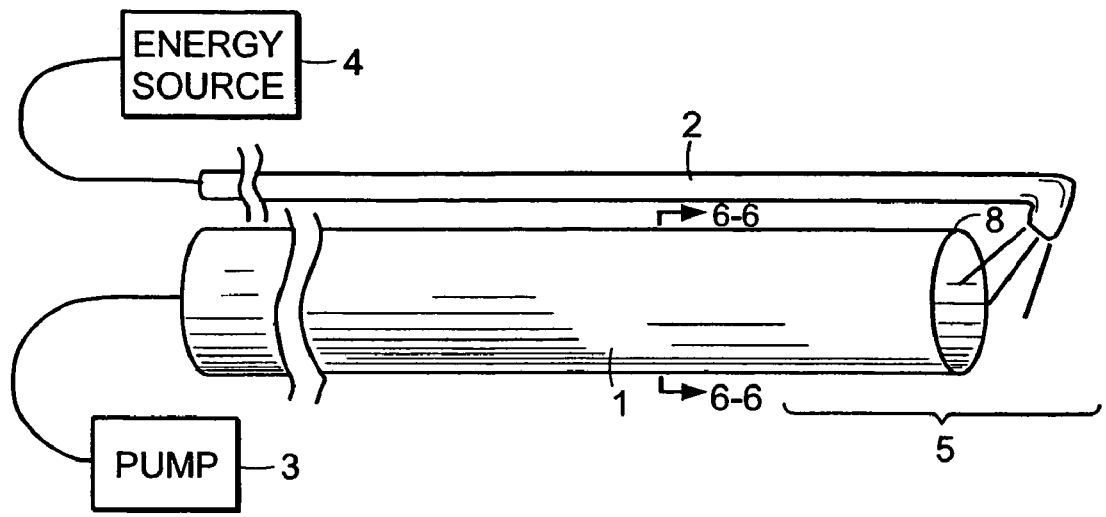
FIG. 1A is a perspective view of an embodiment of a medical device with two conduits configured in accordance with the subject invention.
Figure 1B:
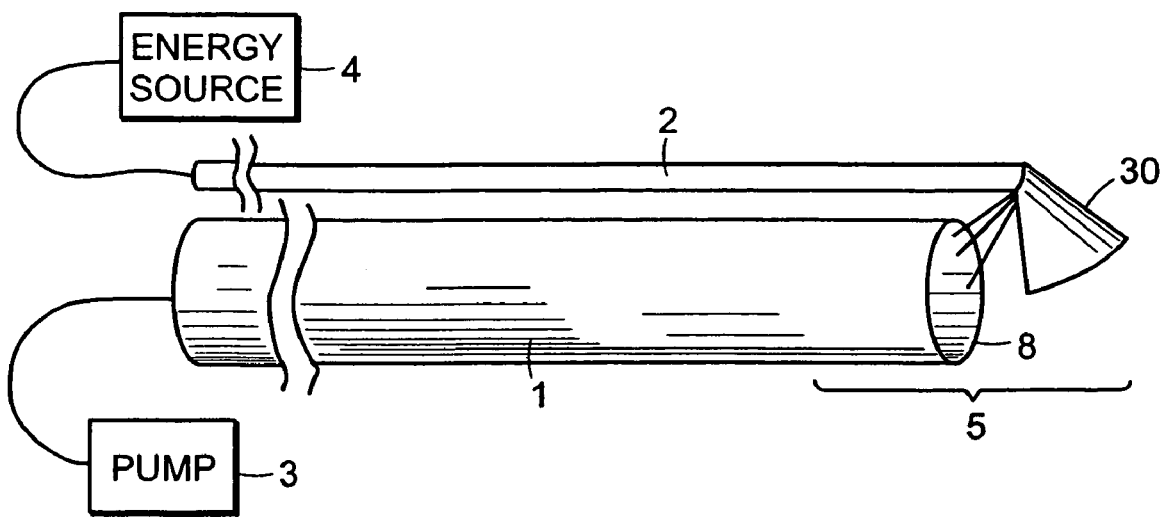
FIG. 1B is a perspective view of an embodiment of a medical device with two conduits and an energy-directing apparatus configured in accordance with the subject invention.

Referring to FIGS. 1A and 1B, an embodiment of the devices of the present invention comprises a suction conduit 1 and an energy-transmitting conduit 2. The suction conduit 1 is connected at its proximal end to a pump 3 that creates a vacuum. The energy-transmitting conduit 2 is connected at its proximal end to a high-energy source 4 and transmits and directs the high energy to the distal region 5 of the suction conduit 1. The suction conduit 1 and the energy-transmitting conduit 2 can be co-extruded, otherwise attached to each other or remain separate. Further, one can be inside the other. Directing the high energy to the distal region 5 may be achieved without additional apparatuses, as in FIG. 1A, or may involve at least one additional optical apparatus 30, as illustrated in FIG. 1B.

The suction conduit can be made of a variety of flexible or rigid materials or a combination of both, such as stainless steel or plastics. To improve conduit's resistance against kink-formation or against collapse under vacuum pressure, and to preserve flexibility in the meantime, either or both of the conduits can be braided or wound with fibers made of materials such as metals or plastics. The conduit may have coatings on its inside or outside for various purposes, for example, for protection against corrosion by body fluids or for insulation against the high energy emitted towards its distal region. It can be of any dimension convenient for its intended use. It can be further inside a housing or a sheath. It can house the energy-transmitting conduit by itself. It can be fixedly integrated into a larger instrument or slidingly inserted into the instrument such as described in U.S. Pat. No. 4,146,019 to Bass et al., incorporated herein by reference. A stainless steel conduit can be passed through a rigid endoscope. A suction conduit made of a flexible material (such as plastic or a super elastic alloy such as Nitinol) can be passed through a flexible endoscope. A preferred embodiment is an elongated polypropylene tubing of ⅛ inch outside diameter that can be used in an endoscope. The devices of the invention may include multiple suction conduits.

The proximal end of the suction conduit is connected to a pump 3, which provides a vacuum when operated. A control mechanism can be further added to the system to modulate the intensity of the vacuum.

The distal end 8 of the suction conduit 1 may assume any shape convenient for its intended use. For example, a suction conduit 1 may have a planar face 7 at its distal end, as depicted in FIGS. 2A and 2B. In FIG. 2B, the face 7 of the distal end is at a beveled angle to the conduit 1's longitudinal axis. The face 7 may also assume a curved form, for example, ellipsoidal as shown in FIG. 2C. Alternatively, as shown in FIG. 2D, the suction conduit 1's distal end may contain at least one side aperture 39. Configurations of the distal end such as those in FIGS. 2B–2D will effectively provide at least one side opening, resulting in direct flow 41 from both the side and the front of the suction conduit 1. Where the devices of the invention are used to remove materials from the walls of a body lumen, embodiments having side openings are preferable, because these side openings readily access target materials, avoiding having to bend the tip. Furthermore, the distal end of the suction conduit can be made of a material different from the body of the conduit. For example, one might want to make the distal end with a more heat-resistant material to withstand high energy directed to it. It may also be desirable to use a more impact-resistant material to withstand the initial impact from stones drawn by the suction force.

Additional structures at the distal region may help prevent clogging of the suction conduit. For example, a filter, a screen, a mesh, a shield or other barriers can be molded onto or otherwise attached to the distal region of the suction conduit. Referring to FIG. 2E, a mesh 9 is attached onto the distal end 8 of the suction conduit 1. The mesh 9 may be placed further inside or outside the distal end 8. Alternatively, several such barriers may be placed along the length of the suction conduit 1.

Figure 2F:
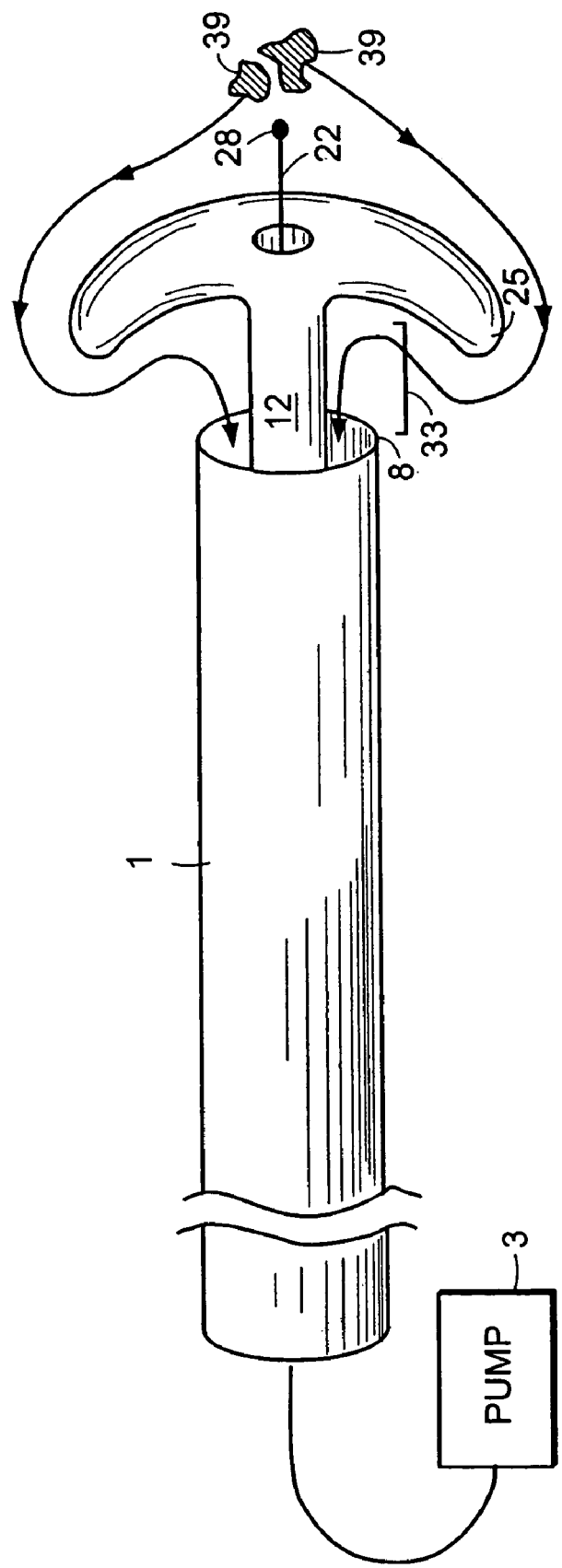
FIG. 2F is a perspective view of an embodiment of a device with a curved barrier at the distal end of the suction conduit in accordance with the subject of the invention.

FIG. 2F shows an example of a barrier positioned outside the distal end of the suction conduit. A channel 12 enclosing an energy-transmitting conduit (a laser fiber 22 in this case) is inserted directly in the suction conduit 1. The distal end of the channel 12 is a curved barrier 25, forming a cap over the distal end 8 of the suction conduit 1, and leaving a gap 33 preferably for about 1–10 mm. The gap 33 is set to admit stone fragments having a size smaller than the suction conduit 1 or than the space between the suction conduit 1 and the channel 12. The distal end 28 of the laser fiber 22 is disposed in the distal region of the channel 12. In the particular embodiment in FIG. 2F, the end 28 is outside the barrier 25, but it can be flush with or receded closely inside the barrier 25. Also, there may be multiple laser fibers enclosed in the channel 12. The barrier 25 can be made of any solid material that can withstand the energy emitted from the distal end 28 and be of sufficient hardness to withstand the impact of stones drawn by the suction force. The barrier 25 is preferably made of light-transmitting materials such as glass or quartz so that it acts as a lens for the laser emitted from the tip 28. The tip 28 can be inside, flush with or outside the barrier 25 and it may be modified, as detailed in later sections, to diffuse or deflect light side-wise or backward. Once the pump 3 is in use, fluid flow will direct mobile particles, such as stone fragments 39, towards the periphery of the barrier 25 and away from the fiber tip 28. As a result, particles must go through the gap 33 between the barrier 25 and the distal end 8 to enter the suction conduit 1. The size of barrier 25 can vary as long as the gap 33 is narrow enough to effectively prevent clogging of the suction conduit. In embodiments where the energy-transmitting conduit is closely receded inside the barrier 25, the large surface area of the barrier exposed to the flow of liquid will help cooling the barrier off rapidly.

The invention contemplates energy sources known to one of ordinary skills in the medical profession for fragmenting, coagulating, or vaporizing various unwanted materials from a body lumen. Such an energy could be mechanical, electric, chemical or a combination thereof. The energy may be delivered in the form of heat, electric current, sparks, laser radiation, radio frequency (RF), ultrasonic wave, mechanical vibrations, ballistic impact, hydraulic shock or chemical corrosives. These techniques are well known in the art and are described in publications, such as U.S. Pat. No. 5,281,231 to Rosen et al. and U.S. Pat. No. 5,443,470 to Stern et al., and "The Swiss Lithoclast: a New Device for Intracorporcal Lithotripsy" by Denstedt et al. in September 1992's *The Journal of Urology*; the entirety of all three are incorporated herein by reference.

In a preferred embodiment, the energy is laser energy with a wavelength that is highly absorbable in a liquid medium. Typically such wavelength regions are the mid-infrared portion of the spectrum from about 1.4 to about 11 micrometers and in the ultraviolet pollution of 190–350 nanometers. Lasers which can be utilized in the present invention are thulium (Th), holmium (Ho), Erbium:yttrium-aluminum-garnet (Er:YAG), HF, DF, CO, and $CO_2$ in the mid-infrared region, and excimer lasers in the ultraviolet region.

In a preferred embodiment, Ho:YAG laser is utilized. The holmium laser is useful because it produces fine dust and small debris rather than stone chunks, and thus facilitates removal of the stone. The Ho:YAG laser can be used not only for the treatment of calculus, but also for soft tissue. The holmium laser energy is typically transmitted through a fiber. When a holmium laser, after travelling the length of the fiber, is fired into a liquid medium the laser energy produces a vaporization bubble.

The Ho:YAG laser produces light at a wavelength of 2.0 to 2.1 microns, depending on the precise formulation of the holmium rod, in a pulsed fashion. In one configuration, the laser produces light at a wavelength of 2.09 microns. These wavelengths are well absorbed by water and other liquid mediums. All stones in a body lumen (including cystine calculi) absorb this wavelength well, regardless of the stone color because of the water in the stone and on the stone surface. This is a major improvement over previous user sources such as pulsed dye laser, the effectiveness of which depends on pigmentation on the target. The pulse duration of Ho:YAG laser also produces photoacoustic effects that aid stone fragmentation. In a particular embodiment, the Sharplan 2025 Holmium:YAG Surgical Laser is utilized as a source of laser energy.

In suitable laser systems, the energy of each pulse and the pulsation frequency can be varied. Generally, high frequency of pulsation and high energy produce a quick fragmentation but also produces a significant amount of stone mobility. Lower frequency of pulsation and lower energy is more precise but the overall treatment time is prolonged. High frequency of pulsation and high energy can be used by the devices of the present invention because the suction force limits stone movement. By combining suction with a laser delivery system in accordance with the methods of the invention, the overall efficiency of treatment is improved. In particular, higher powers, more efficient lasers, such as holmium lasers, can be used even when small stones are present because the suction helps keep the small stones in the path of the laser. Preferably, the energy levels used as between about 0.2 and 2.8 Joules per pulse and the frequency is between about 5 and 20 Hertz. Typical pulse durations are about 200–400 microseconds. Preferably, the pulse duration is 250 microseconds.

Referring again to FIGS. 1A and 1B, a high-energy source 4 is connected to the proximal end of the energy-transmitting conduit 2. This conduit 2 should be made of a material that is suitable for the transmission of the energy used in the device and variables of its dimension (such as length, diameter and shape) should be suitable for the intended use of the device. It can be further inside a housing or a sheath, such as the suction conduit itself. The invention can have more than one conduit transmitting the high energy. Some or all of them can be fixedly integrated into a larger instrument or slidingly inserted into an instrument.

In a preferred embodiment, this energy-transmitting conduit is a low density, optical quartz fiber that can be used to transmit laser energy. Generally, the laser fiber extends from about 50 to 500 cm. Preferably, the laser fiber extends from about 80 to 100 cm. These fibers range in their core size from about 200 to 1000 microns. Preferably the core size of the laser fiber is between 300 and 550 microns.

In another embodiment, the medical device comprises a plurality of mobile components within a housing, and at least one of the mobile components has a discernable pattern of indicia disposed on the outer surface of its distal region. The plurality of mobile components may be at least two of any components of a medical device used in a body lumen, including but not limited to, laser fibers, fiber optics, catheters and guidewires.

Figure 3A:
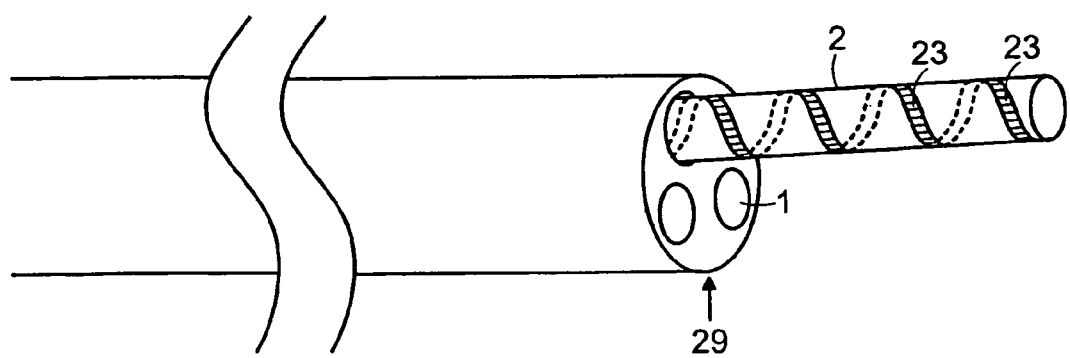
FIG. 3A is a perspective view of an embodiment of a device with an energy-transmitting conduit that has endoscopically discernable external markings in accordance with the invention.
Figure 3B:
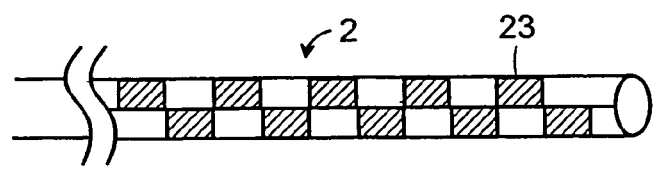
FIG. 3B is a perspective view of an embodiment of an energy-transmitting conduit with an alternative marking pattern in accordance with the invention.

For example, in FIGS. 3A and 3B, the energy-transmitting conduit 2 is a laser fiber jacketed with a pattern of indicia 23 that aids detection of its movement inside a body lumen through a viewing instrument. An example of a viewing instrument is an endoscope that contains a fiber optic illumination source and a fiber optic lens for viewing. Typically, the scope view 29 shows a small section of the laser fiber near the fiber's distal end. However, commercially available laser fibers generally have no distinguishing marking on the outside—they are generally jacketed in a monochromatic (e.g., black) and glossy plastic wrapping. One aspect of the invention is to provide discernable markings or indicia 23 for the energy-transmitting conduit and other mobile components in the device. The markings only needs to appear on the section that is to be seen through the viewing instrument—in the case of an endoscope, the distal region of the fibre visible under the scope view 29. The spiral and checkered patterns, as shown in FIGS. 3A and 3B respectively, are examples of preferred embodiments because these patterns indicate, in the scope view 29, conduit movements both along and about the longitudinal axis. Further, the energy-transmitting conduit and any tubular components (such as a guidewire) viewable through the endoscope should have different markings for the user to tell them apart. This can be accomplished through different colors or patterns. This inventive aspect contributes to the overall goal of the invention when movements of the components are desired for operating the device or the movements actually take place, and where direct visual monitoring of such movements will aid the operation of the device.

To make components of the devices further discernable when combined with a viewing instrument such as an endoscope, a non-reflective or low-reflective coating as a pattern of indicia can be applied to these conduits to soften light reflected from them. In an endoscope with a means of illumination, the light is often so intense that the user finds it difficult to view through the viewing instrument. A coating that reduces light reflection from the laser fiber jacket, for instance, will solve that problem.

Figure 3C:
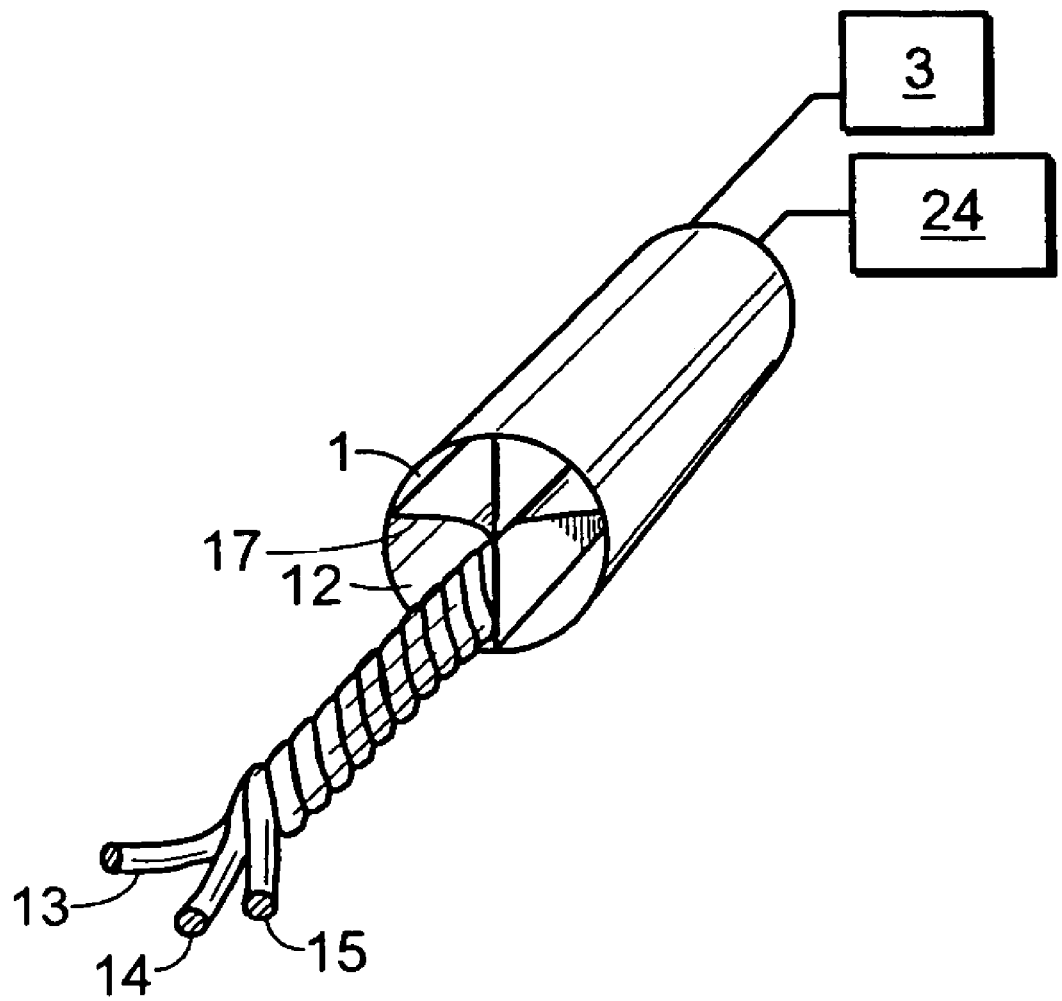
FIG. 3C is an elevated perspective view of an embodiment of a medical device with a twisted bundle of laser fibers in accordance with the invention.

Referring to FIG. 3C, multiple laser fibers 13–15 are housed in a channel 12 of a larger instrument, such as an endoscope and the arranged fibers provide markings, as a whole, that are endoscopically discernable. There can be a variety of ways of bundling multiple conduits, such as spirally twisting the bundle (as in FIG. 3C), braiding into a bundle, gluing, tying or fitting tightly into a channel of a housing. Twisting, braiding or otherwise tightening the association of multiple fibers retains much of the flexibility of individual fibers. It is easier to move bundled fibers than unbundled ones inside a housing, whether along or about the housing's longitudinal axis. In a preferred embodiment, each of the three fibers is jacketed in a sleeve of a different color, forming an overall spiral pattern when inserted into an endoscope. The same principle applies to other numbers of energy-transmitting conduits as long as endoscopically discernable patterns are provided by the overall bundle.

Directing at least a portion of the energy emitted towards the distal region of the suction conduit can be accomplished with the laser fiber itself as an integral optical feature or with a separate optical apparatus.

Figure 4:
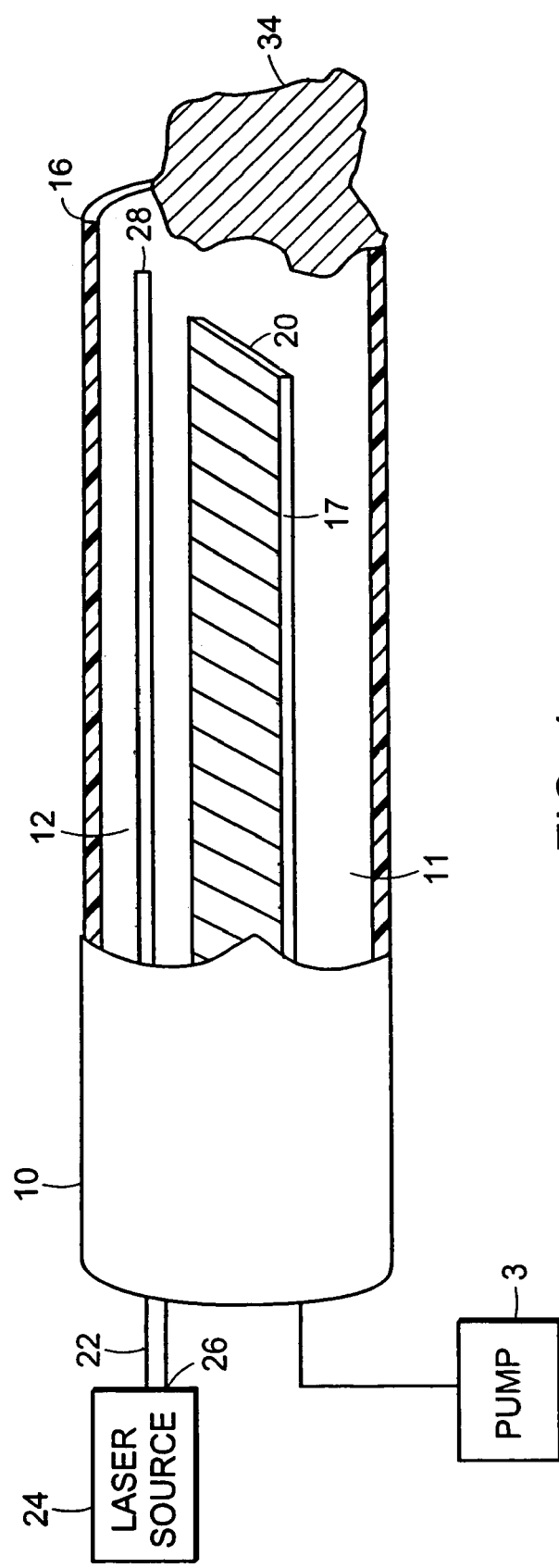
FIG. 4 is a partly cross-sectional view of an embodiment of a laser lithotripsy device with housing configured in according with the invention.

For example, spatial relationship between the two conduits is one solution. In FIG. 4, a suction conduit, channel 11, is integral to an instrument 10 that houses a laser-transmitting fiber 22 inside its other channel 12. A divider 17 having a distal end 20 partly separates channel 11 from channel 12. The housing 10 has a distal end 16 that comes into contact with a stone 34 that is to be removed. The laser fiber 22 is connected to a laser source 24 at its proximal end 26. The laser fiber 22's distal tip 28 is close to both the distal end 16 of the housing 10 and the distal end 20 of the divider 17, so that stones caught at either of the distal ends 16 and 20 can be exposed to laser radiation emitted from tip 28.

In the particular embodiment shown in FIG. 4, both the laser fiber's distal tip 28 and the divider 17's distal end 20 are disposed within the distal end 16 of the housing 10. This illustration is not meant to put any structural limit on the devices of the invention. In other embodiments, both or either of the distal tip 28 and the distal end 20 may be flush with the distal end 16 of the housing or may extend beyond it so long as at least a portion of the laser radiation from tip 28 can effectively fragment a stone caught at the distal region of the suction conduit 11.

Figure 5A:
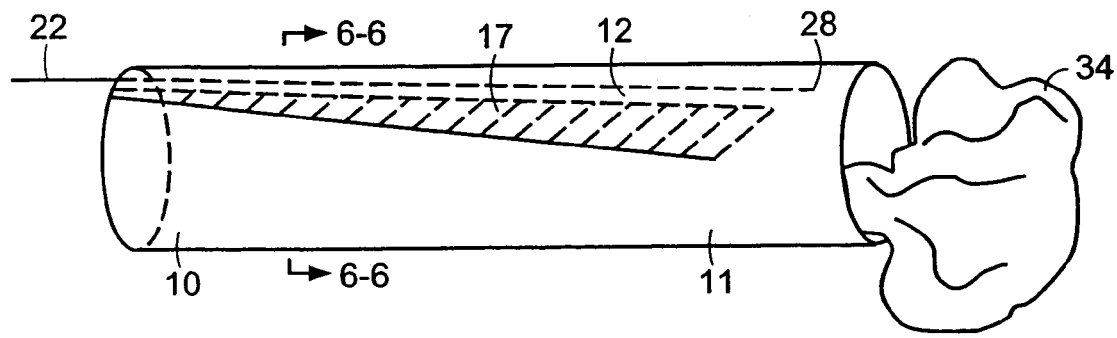
FIG. 5A is a perspective view of an embodiment of a device with a multi-channel housing configured in accordance with the invention.
Figure 5B:
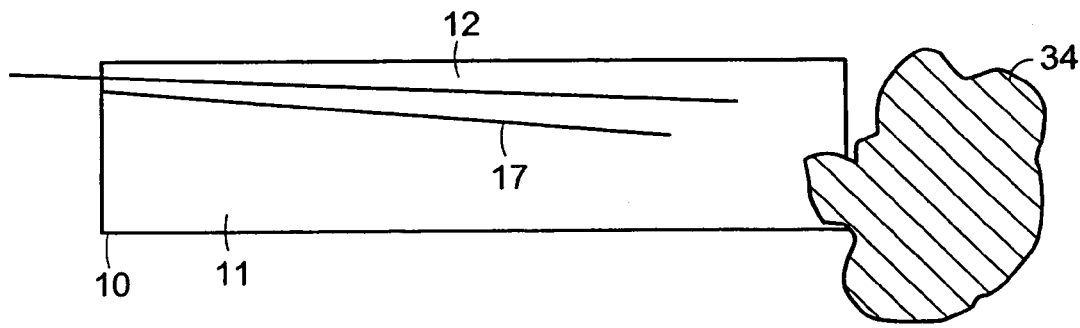
FIG. 5B is a longitudinal cross-section view of the device in FIG. 5A taken along line 6—6 in FIG. 5A.

In FIGS. 5A–5B, the divider 17 is positioned so that it facilitates the placement of a laser fiber 22 at a beveled angle with the longitudinal axis of the housing 10, thereby directing laser radiation emitted from tip 28 of the energy-transmitting conduit 22 towards the distal region of suction conduit 11. Furthermore, because the diameter of the suction conduit increases towards its proximal end, clogging along the body of the suction conduit is prevented.

Figure 6A:
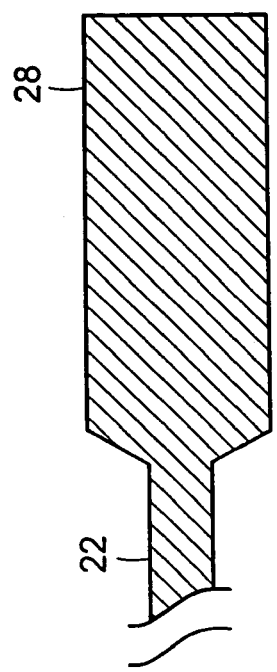
FIGS. 6A–6C are schematic views of modified distal ends of laser fibers in accordance with the invention.
Figure 6B:
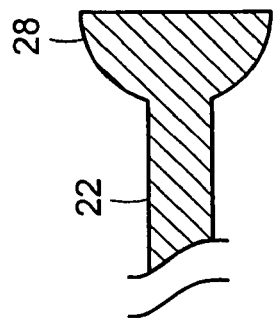
Figure 6C:
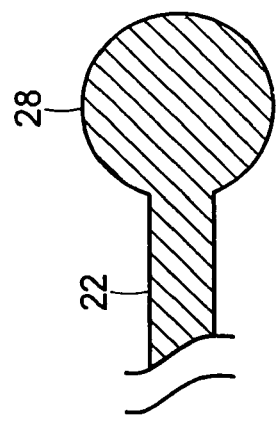

In other embodiments, a portion of the energy emitted from the tip 28 maybe directed towards the distal end of the suction conduit through modifications to the energy-transmitting conduit. For example, the distal end of a typical, commercially available laser fiber can be modified so that a larger surface area will be radiated by the laser. FIGS. 6A–6C disclose examples of modifications with various optical lenses disposed at the laser fiber tips to diffuse the laser energy. These optical lenses are easily manufactured by removing the plastic jacket from the distal region of the fiber, then using a torch to thermally heating up the remaining optical core at the distal end, including its usual silicon clad. The tip will melt, and after cooling off in room temperature, will form a ball as shown in FIG. 6A. If the molten tip is pressed against a nonporous, flat surface at a right angle, a flat-end tip resembling that shown in FIG. 6B will result. Further pressing the same flat surface on the lateral sides of the tip will result in an extended tip resembling what is shown in FIG. 6C. An extended tip, of about 5 mm, is especially advantageous for continued use of the same laser fiber.

Other means of affecting the direction of laser path without resorting to additional apparatus include etching near the distal end of the energy-transmitting conduit or bending the distal tip for side-firing (described in U.S. Pat. No. 5,416,878 and incorporated herein by reference). Cutting at multiple spots in the distal region of a laser fiber results in light emission along the distal region, in addition to the distal end. FIG. 7A provides a specific example of etching, where the distal end 28 of a laser fiber is cut so that an angled tip is formed. In a schematically depicted laser fiber 22, laser light 42 travels along the optical core 37 via bouncing between the silicon clad 36, which is further wrapped in a plastic jacket 35. As shown here, because in the angled tip, one side of the fiber is longer than the other, some of the laser light 42 will be deflected side-wise once it reaches the end of the optical core 37.

Reflective coatings on the laser fiber may also be used to affect the laser path. Referring to FIG. 7B, a portion of the distal region of the laser fiber 22 has been stripped of the plastic jacket 35 and the silicon clad 36 (therefore "unclad"), and at least one layer of reflective coating 50 has been selectively applied, to the remaining unclad optical core, including the distal face 48. The reflective coating 50 is not applied to certain areas on the unclad optical core so..that reflected laser light can "escape" from these areas and reach a target such as the distal region of the suction conduit. Depending on the effectiveness of the coatings, however, some of the light might still go through the coated areas.

An optic, separate from the energy-transmitting conduit may be placed near the distal end of the energy-transmitting or of the suction conduit to help direct the emitted energy towards the distal region of the suction conduit. In preferred embodiments where the energy is a Ho:YAG laser, the devices of the invention include an optical apparatus.

Several optics known in the art that guide laser emission to a certain area can be used in the invention. They can be a surface, a series of surfaces, a medium, a series of media, or a combination of any of the above that alters the path of light. For example, a light diffusing apparatus is described in U.S. Pat. No. 5,151,096 to Khoury, incorporated herein by reference. Examples of other optics include and are not limited to a lens, a mirror (U.S Pat. No. 4,445,892). a series of mirrors (U.S. Pat. No. 5,496,306), a prism (U.S. Pat. No. 5,496,309) and a parabolic reflector (U.S. Pat. No. 4,672,961) (the disclosure of these patents are incorporated herein by reference).

Figure 8A:
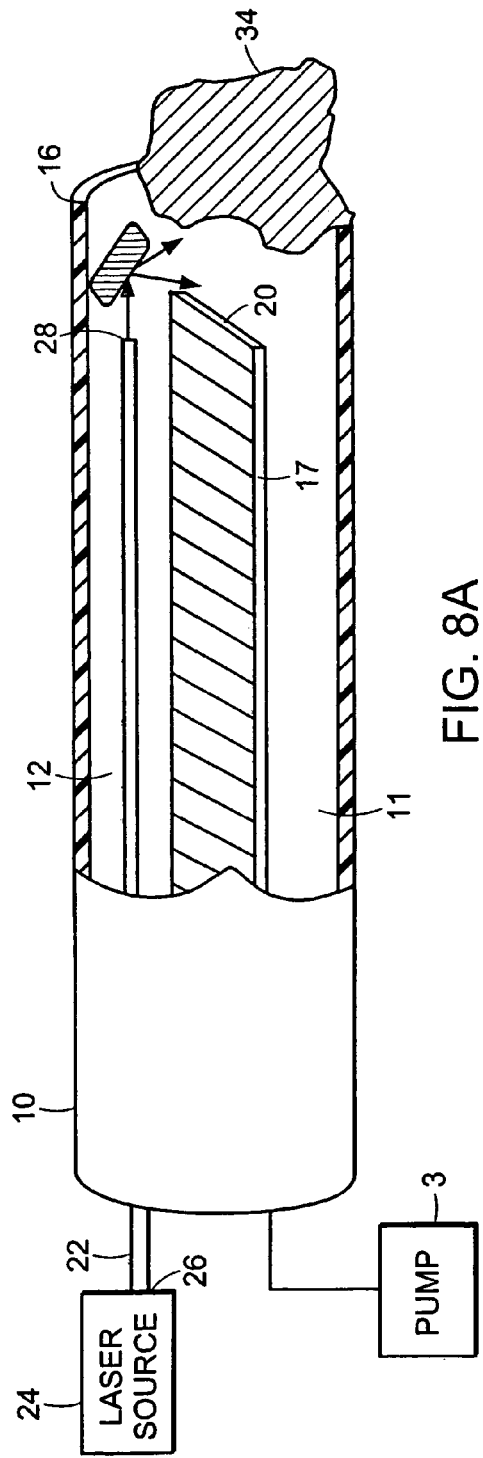
FIGS. 8A–8B are partly cross-sectional views of embodiments of a laser lithotripsy device with an optical apparatus configured in accordance with the invention.
Figure 8B:
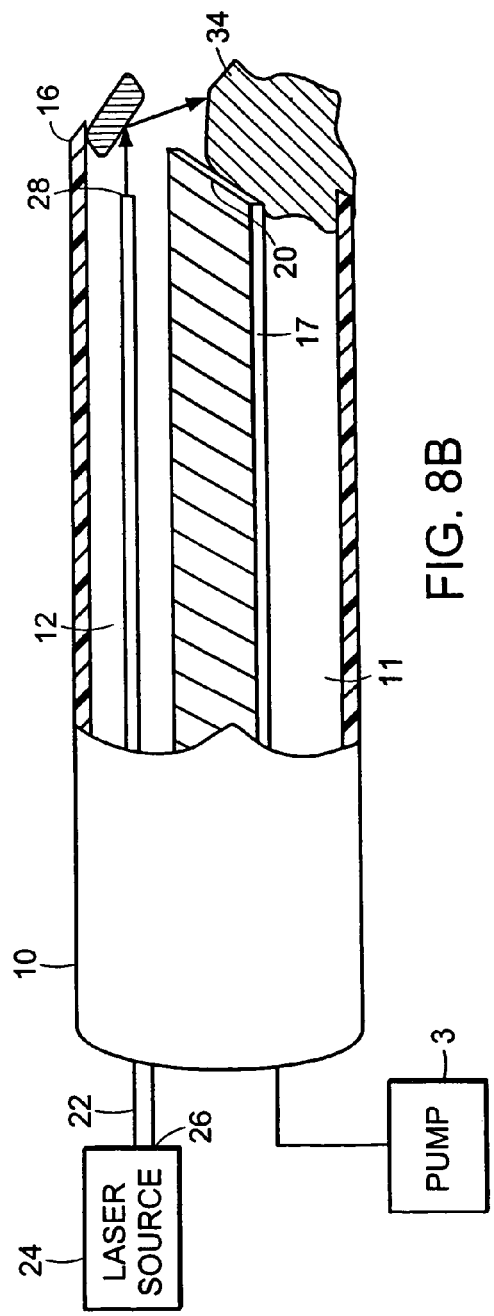

In the present invention, the optical apparatus is operatively associated with the two conduits to help direct laser light from the distal end of the energy-transmitting conduit toward the distal region of the suction conduit. In FIGS. 8A–8B, an embodiment has an optical apparatus 30 coupled near the distal end 16 of a housing similar to that shown in FIG. 4. In the embodiment shown in FIG. 8A, the divider 17 is receded proximal to the optical apparatus 30, which, in turn, is receded inside the distal end 16 of the housing 10. In the embodiment shown in FIG. 8B, the divider 17 extends all the way to the distal end 16 of the housing 10, and the optical apparatus 30 is also positioned more outward. The angle of the optical apparatus 30 may be varied to direct a larger portion of the energy emitted from the laser fiber 22 inside, across or outside the face of the distal end 16.

The optical apparatus 30 can be made of a variety of materials that are known in the art to be suitable for reflecting, deflecting, diffusing, or refracting the particular energy emitted from the tip 28 of the laser fiber. Such materials include, but are not limited to, crystal, quartz, garnet, stainless steel or gold. The optical apparatus 30 may assume a variety of configurations such as a planar surface, an ellipsoidal surface, a convex surface or a pyramid.

The device with an optical apparatus may utilize Ho:YAG laser energy which produces a vaporization bubble, a semicircle of energy, extending from the tip of a firing laser fiber to a target stone when the laser tip is immersed in liquid. While the body lumen where the device is operating generally has plenty of water, a separate irrigation conduit can be added to the device to ensure that the tip is constantly immersed in water. The optical apparatus 30 in FIGS. 8A and 8*b* directs the vaporization bubble (not shown) into the distal region of the suction conduit 11 and onto the stone 34. A shock-wave is then produced by the collapse of the vaporization bubble at the interface between water and the stone.

Figure 9:
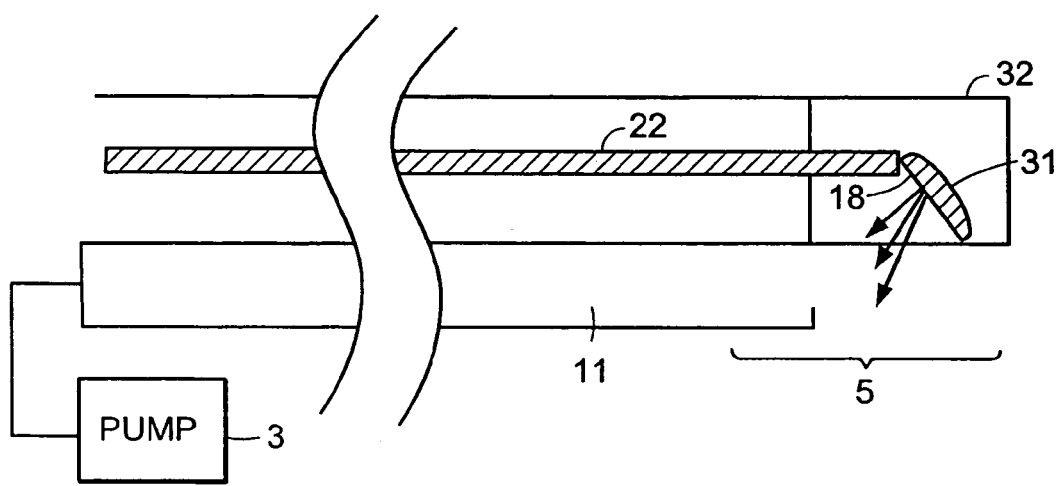
FIG. 9 is a schematic longitudinal cross-section view of an embodiment of the invention with an optical apparatus.

Referring to FIG. 9, another preferred embodiment of the device has a reflective surface 31 (a mirror, for example) fixedly attached to the distal end of an energy-transmitting conduit (a laser fiber 22 in this case). A housing 32 preferably made with a light-transmitting hard material such as quartz, fixedly encloses the distal region of the laser fiber 22. The housing 32 protects the laser fiber 22 and acts as a lens for the laser. Laser energy emitted from distal end 18 of fiber 22 is reflected by the reflective surface 31 and travels through the housing 32 to the distal region of the suction conduit 11. Alternatively, the housing can be made of an opaque material with an opening for the laser light to travel to the distal region 5 of the suction conduit 11.

Different embodiments and various features of the invention can be combined in the same device in accordance with the invention. An embodiment may contain multiple optical features and any of the distal barriers mentioned earlier. For example, multiple laser fibers modified with an optical lens-tip as illustrated in FIGS. 6A–6C, and braided together as shown in FIG. 3, may be disposed inside the distal end of the barrier 25 of the device shown in FIG. 2F—the barrier 25 is made of glass, quartz or sapphire and serves as a lens at the same time.

Figure 10A:
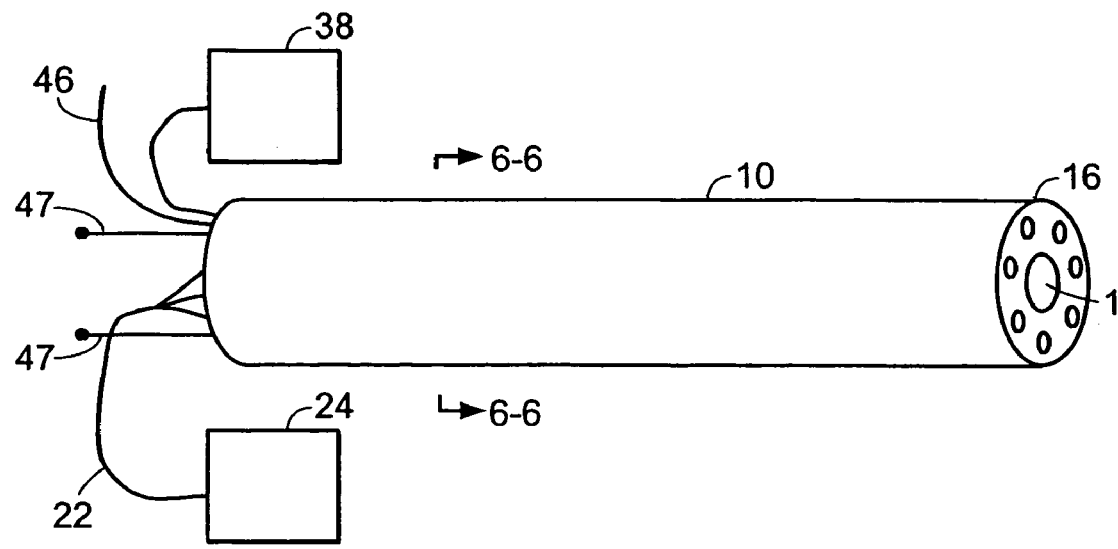
FIG. 10A is a perspective view of an embodiment of a device with multiple channels for laser fibers surrounding a suction conduit.
Figure 10B:
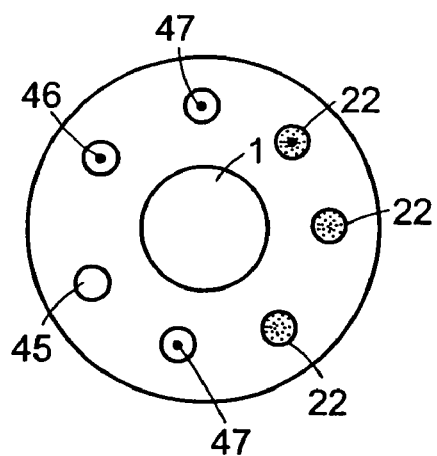
FIG. 10B is a radial cross-section view of the device in FIG. 10A taken along line 6—6 in FIG. 10A.

There are several ways to direct a larger portion of emitted energy towards the distal region 5 of the suction conduit. In one embodiment, the diameter of the energy-transmitting conduit is increased. In other embodiments, an optical apparatus is added. Alternatively, more energy-transmitting conduits can be incorporated into the device. In a preferred embodiment, these conduits are intertwined and bundled before being incorporated into the device. Again, all these measures can be implemented in the same embodiment. In another preferred embodiment shown in FIGS. 10A and 10B, multiple energy-transmitting conduits such as multiple laser fibers 22 are housed in multiple channels of a housing 10. In this particular embodiment, these channels surround the suction conduit 1. Some of the channels may enclose other functional components. As shown in FIGS. 10A and 10B, one of the channels is an irrigation channel 45, which transfers a cooling agent from an irrigation source 38. Another channel contains a guidewire 46. Two other channels each contain a pullwire 47. A pullwire is a wire fixedly attached to the distal end 16 of an endoscopic instrument and a user can deflect the distal end 16 upon pulling such a wire.

The devices of the invention may be combined with, or incorporated into, a catheter, an endoscope or other medical devices customarily used for the destruction and removal of unwanted materials from body lumens. Preferably, when incorporated into an endoscope, the devices of the invention combine a guidewire, a fiber optic for illumination, a fiber optic or visualization, a conduit for irrigation and pullwires for active deflection.

The devices of the invention have applications in lithotripsy. In the methods of the invention, the device 10 shown in FIGS. 10A and 10B, is placed with its distal end 16 in the vicinity of a calculus. Upon application of vacuum in the suction conduit 1, the suction pulls large stone fragments toward the distal end 16 of the housing. 10. The laser system 24 delivers laser energy to the tip of the laser fibers 22. The laser energy is then emitted from the tip of the laser fibers 22. The laser energy may be in the form of a vaporization bubble. Optionally, an optical apparatus further directs the laser energy released from the laser fiber 22 into, across the face of, and/or outside of the suction conduit 1 and onto a stone. The laser energy impacts the stone caught by the suction at the distal region of the suction conduit 1, causing it to be propelled off the tip and fragmented into smaller stone fragments. The suction then pulls the smaller fragments back into the distal region of the conduit 1. Fragments small enough will enter the suction conduit and be evacuated from the treatment site. Large fragments still be held at the distal end of the suction conduit. The laser energy impacts the stone fragment causing it to be propelled off the tip and fragment into even smaller fragments. This process is repeated until the stone fragments are small enough to be all evacuated through the suction conduit 1. Directing at least some of the laser energy into the suction conduit 1 keeps, the conduit clear of obstruction.

In addition to removing stones, the devices of the invention can be utilized to remove soft tissue, for example, to facilitate the treatment of tumors or soft growths in both the gastrourinary (GU) and the gastrointestinal (GI) tract. Specifically, the devices can be utilized to shear off and evacuate soft tissue such as polyps. Papillary lesions can be fragmented and evacuated while the base of the lesion is coagulated.

Figure 11:
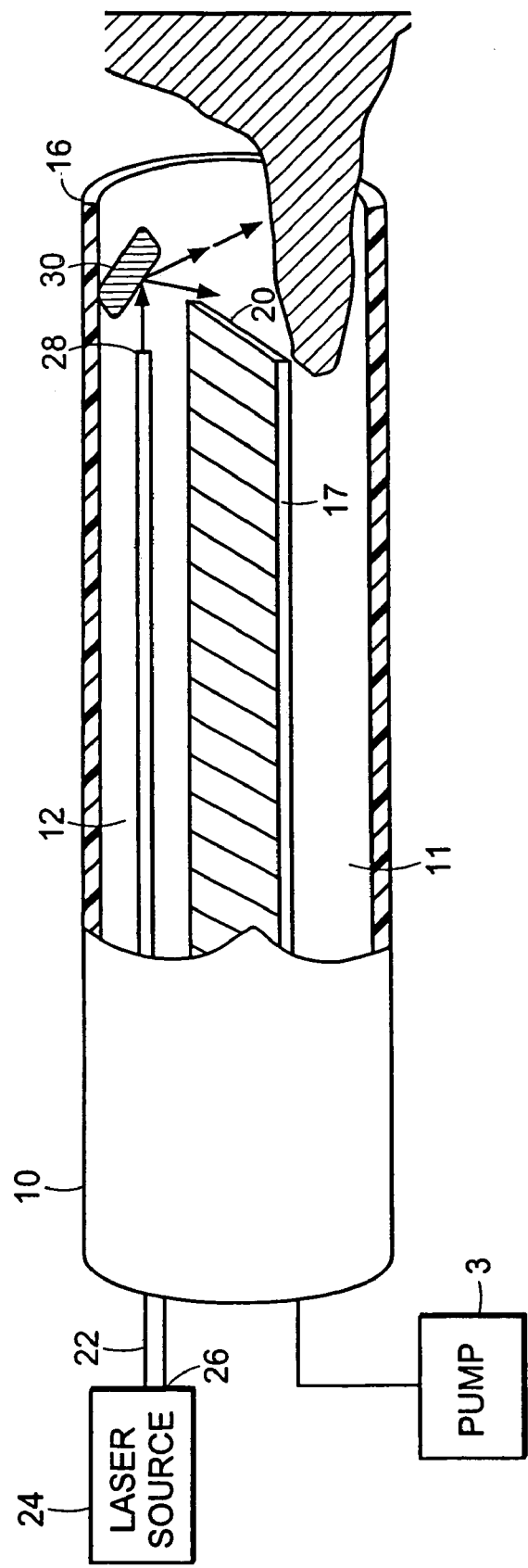
FIG. 11 is a schematic view of a tissue-removing device with an optical apparatus in accordance with an embodiment of the invention.

In one embodiment for treatment of soft tissue, illustrated in FIG. 11, the laser lithotripsy device is modified to facilitate the removal of polyps. The tip 28 of the laser fiber 22 and the optical apparatus 30 attached to the distal end 16 are both disposed within the channel 12 about 2 millimeters from the distal end 16. Soft tissue 40 such as a polyp or tumor is sucked into the suction channel 11, is sheared off by the laser energy emitted by the laser fiber 22, and then is evacuated by the suction. The angle of the optical apparatus 30 may be varied to change the direction of the laser energy emitted from the tip 28. The laser lithotripsy device with an angled laser fiber tip but without a separate optical apparatus may also be modified to accommodate soft tissue by moving the tip 28 of the laser fiber 22 further within the channel 12 several millimeters from the distal end 16. Alternatively, the device can be equipped with fluoroscopic guidance so that the laser can be directed onto the polyp or tumor.

Variations, modifications, and other implementations of what is described herein will occur to those of ordinary skill in the art without departing front the spirit and the scope of the invention as claimed. Accordingly, the invention is to be defined not by the preceding, illustrative description but instead by the spirit and scope of the following claims.

What is claimed is:

1. A medical device comprising:
   a suction conduit capable of removing material from a body lumen and configured to provide suction at a distal region of the medical device;
   an optic fiber configured to transmit energy capable of fragmenting, coagulating, or vaporizing material in a body lumen, at least a portion of energy transmitted being directed towards a distal region of the suction conduit; and
   a barrier positioned beyond a distal end of the suction conduit, such that a gap is formed between the barrier and the distal end of the suction conduit; the barrier including a channel housing the optic fiber;
   wherein the size of the gap is configured to limit the size of objects removed through the suction conduit.

2. The medical device of claim 1, wherein the optic fiber comprises a plurality of optic fibers intertwined together in a bundle.

3. The medical device of claim 1, wherein the optic fiber comprises an optical core of a material composition, the material composition forming an enlarged distal end of the optic fiber.

4. The medical device of claim 1, wherein the optic fiber has an angled tip.

5. The medical device of claim 1, wherein a distal region of the optic fiber comprises an unclad optical core and a reflective coating.

6. The medical device of claim 1, wherein a distal region of the optic fiber defines at least one side window to allow emission of the energy.

7. The medical device of claim 1, wherein the source of energy is a holmium laser.

8. The medical device of claim 1, wherein the barrier is formed of a light transmitting material that acts as a lens for the optic fiber.

9. A medical device comprising:
   a suction conduit capable of removing material from a body lumen and configured to provide suction at a distal region of the medical device;
   an energy transmitting conduit configured to transmit energy capable of fragmenting, coagulating, or vaporizing material in a body lumen, at least a portion of energy transmitted being directed towards a distal region of the suction conduit;
   a channel, inserted in the suction conduit, extending along the medical device and enclosing the energy transmitting conduit; and
   a barrier positioned beyond a distal end of the suction conduit such that a gap is formed between the barrier and the distal end of the suction conduit, the barrier housing a portion of the energy transmitting conduit;

wherein the size of the gap is configured to limit the size of objects removed through the suction conduit.

10. The medical device of claim 9, wherein the barrier is formed at a distal end of the channel and the channel extends through the barrier.

11. The medical device of claim 10, wherein a distal end of the energy transmitting conduit extends beyond the channel outside the barrier.

12. The medical device of claim 10, wherein the distal end of the energy transmitting conduit is disposed proximal to the distal end of the channel.

13. A medical device comprising:
   a suction conduit capable of removing material from a body lumen and configured to provide suction at a distal region of the medical device;
   an energy transmitting conduit configured to transmit energy capable of fragmenting, coagulating, or vaporizing material in a body lumen, at least a portion of energy transmitted being directed towards a distal region of the suction conduit; and
   a barrier positioned outside a distal end of the suction conduit such that a gap is formed between the barrier and the distal end of the suction conduit;
   wherein the barrier has a curved shape forming a cap at the distal region of the suction conduit; and
   wherein the size of the gap is configured to limit the size of objects removed through the suction conduit.

14. A medical device comprising:
   a suction conduit capable of removing material from a body lumen and configured to provide suction at a distal region of the medical device;
   an energy transmitting conduit configured to transmit energy capable of fragmenting, coagulating, or vaporizing material in a body lumen, at least a portion of energy transmitted being directed towards a distal region of the suction conduit;
   a barrier positioned outside a distal end of the suction conduit such that a gap is formed between the barrier and the distal end of the suction conduit;
   wherein the size of the gap is configured to limit the size of objects removed through the suction conduit; and
   a discernable pattern of indicia disposed on a distal end portion of the energy transmitting conduit and configured to aid an operator in positioning the energy transmitting conduit during a medical procedure.

15. The medical device of claim 14, wherein the indicia comprises a spiral pattern.

16. The medical device of claim 14, wherein the indicia comprises a checkered pattern.

17. The medical device of claim 14, wherein the energy transmitted is of at least one of the following forms: heat, electricity, light, sound, radio frequency, mechanical force or chemical agent.

18. A medical device comprising:
   a suction conduit capable of removing material from a body lumen and configured to provide suction at a distal region of the medical device;
   an elongated housing having a plurality of channels extending along the medical device and radially separated from the suction conduit;
   at least one energy transmitting conduit housed within one of the plurality of channels and configured to transmit energy capable of fragmenting, coagulating, or vaporizing material in a body lumen, at least a portion of energy transmitted being directed towards a distal region of the suction conduit; and
   an optic disposed near the distal end of at least one energy transmitting conduit to assist directing energy toward a distal region of the suction conduit.

19. The medical device of claim 18, wherein one of the plurality of channels is an irrigation channel which transfers a cooling agent from an irrigation source.

20. The medical device of claim 18, wherein one of the plurality of channels houses a guidewire.

21. The medical device of claim 18, wherein two of the channels each house a pullwire connected to a distal end of the medical device configured to enable deflection of the distal end of the medical device.

22. The medical device of claim 18, further comprising multiple energy transmitting conduits each conduit housed within a separate channel of the plurality of channels of the medical device.

23. The medical device of claim 18, wherein the optic comprises a lens.

24. The medical device of claim 18, wherein the optic comprises a reflective surface.

25. The medical device of claim 18, wherein the energy transmitted is of at least one of the following forms: heat, electricity, light, sound, radio frequency, mechanical force or chemical agent.

26. A medical device comprising: a suction conduit capable of removing material from a body lumen and configured to provide suction at a distal region of the medical device;
   an elongated housing having a plurality of channels extending along the medical device and radially separated from the suction conduit;
   at least one energy transmitting conduit housed within one of the plurality of channels and configured to transmit energy capable of fragmenting, coagulating, or vaporizing material in a body lumen, at least a portion of energy transmitted being directed towards a distal region of the suction conduit; and
   wherein the energy transmitting conduit comprises an optic fiber.

27. The medical device of claim 26, wherein the source of energy is a holmium laser.

28. A medical device comprising:
   a suction conduit capable of removing material from a body lumen and configured to provide suction at a distal region of the medical device;
   an elongated housing having a plurality of channels extending along the medical device and radially separated from the suction conduit;
   at least one energy transmitting conduit housed within one of the plurality of channels and configured to transmit energy capable of fragmenting, coagulating, or vaporizing material in a body lumen, at least a portion of energy transmitted being directed towards a distal region of the suction conduit; and
   a discernable pattern of indicia disposed on a distal end portion of at least one energy transmitting conduit and configured to aid an operator in positioning an energy transmitting conduit during a medical procedure.

29. The medical device of claim 28, wherein the indicia comprises a spiral pattern.

30. The medical device of claim 28, wherein the indicia comprises a checkered pattern.

* * * * *

UNITED STATES PATENT AND TRADEMARK OFFICE
CERTIFICATE OF CORRECTION

| | | |
|---|---|---|
| PATENT NO. | : 7,104,983 B2 | Page 1 of 1 |
| APPLICATION NO. | : 10/801128 | |
| DATED | : September 12, 2006 | |
| INVENTOR(S) | : Michael Grasso, III et al. | |

It is certified that error appears in the above-identified patent and that said Letters Patent is hereby corrected as shown below:

Column 12, line 27, "conduit, such" should read --conduit such--.

Column 12, line 28, "conduit; the" should read --conduit, the--.

Column 14, line 14, "conduits each" should read --conduits, each--.

Signed and Sealed this

Twelfth Day of December, 2006

JON W. DUDAS
*Director of the United States Patent and Trademark Office*